United States Patent
McCauley et al.

(10) Patent No.: US 9,816,960 B2
(45) Date of Patent: Nov. 14, 2017

(54) GAS SENSOR AND METHOD OF MAKING

(71) Applicant: DELPHI TECHNOLOGIES, INC., Troy, MI (US)

(72) Inventors: Kathryn M. McCauley, Durand, MI (US); Charles Scott Nelson, Fenton, MI (US); David M. Racine, Davison, MI (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 490 days.

(21) Appl. No.: 14/298,156

(22) Filed: Jun. 6, 2014

(65) Prior Publication Data

US 2015/0354997 A1  Dec. 10, 2015

(51) Int. Cl.
*G01N 27/407* (2006.01)
*B23K 11/00* (2006.01)

(52) U.S. Cl.
CPC ........ *G01N 27/4078* (2013.01); *B23K 11/002* (2013.01); *Y10T 29/49119* (2015.01); *Y10T 29/49828* (2015.01)

(58) Field of Classification Search
CPC .................................................. G01N 27/4078
USPC ............................................... 73/431, 23.31
See application file for complete search history.

(56) References Cited

U.S. PATENT DOCUMENTS

| | | | |
|---|---|---|---|
| 5,238,551 A | 8/1993 | Katsu | |
| 6,477,887 B1 | 11/2002 | Ozawa et al. | |
| 6,550,309 B1 * | 4/2003 | Noda | G01N 27/407 204/424 |
| 7,197,912 B1 * | 4/2007 | Duce | G01N 27/4077 73/23.31 |
| 7,341,650 B2 * | 3/2008 | Matsuo | G01N 27/4077 204/426 |
| 7,454,949 B2 * | 11/2008 | Geier | G01N 27/407 204/424 |
| 7,497,109 B2 * | 3/2009 | Satou | G01N 27/4077 73/31.05 |
| 7,563,118 B1 * | 7/2009 | McCauley | H01R 13/533 439/260 |
| 7,811,434 B2 * | 10/2010 | Mizutani | G01N 27/4071 204/424 |
| 7,827,848 B2 | 11/2010 | Kuisell et al. | |
| 2014/0102170 A1 * | 4/2014 | Kato | G01N 27/4078 73/23.31 |

* cited by examiner

*Primary Examiner* — Lisa Caputo
*Assistant Examiner* — Jamel Williams
(74) *Attorney, Agent, or Firm* — Joshua M. Haines

(57) ABSTRACT

A gas sensor includes a metallic shell extending along a shell axis and defining a shell attaching surface that is substantially perpendicular to the shell axis; a metallic shield extending along a shield axis and defining a shield attaching surface that is substantially perpendicular to the shield axis; and a ceramic sensing element extending along a sensing element axis, the sensing element being rigidly fixed at a first axial location of the sensing element to the shell and the sensing element being laterally supported by the shield at a second axial location of the sensing element that is axially spaced apart from the first axial location. The shield is attached to the shell at an interface formed between the shield attaching surface and the shell attaching surface, thereby accommodating misalignment between the shield axis and the shell axis. A method of making the gas sensor is also provided.

20 Claims, 5 Drawing Sheets

GAS SENSOR AND METHOD OF MAKING

TECHNICAL FIELD OF INVENTION

The present invention relates to a gas sensor, more particularly to such a gas sensor which includes a ceramic sensing element mounted in a metallic shell at a first axial position of the sensing element, even more particularly to such a gas sensor which also includes a metallic shield which laterally supports the sensing element at a second axial position of the sensing element such that misalignment between the shell and the shield is accommodated in order to eliminate or minimize stress on the sensing element.

BACKGROUND OF INVENTION

Gas sensors are known for determining composition concentrations in hot gases, for example, combustion exhaust gases produced by an internal combustion engine. A typical gas sensor as shown in U.S. Pat. No. 6,477,887 to Ozawa et al. includes a sensing subassembly joined to an electrical harness subassembly. The sensing subassembly includes a metallic shell with a ceramic sensing element mounted rigidly therewithin at a first axial location of the sensing element. The shell extends along a shell axis while the sensing element extends along a sensing element axis. Due to manufacturing tolerances and variations, the shell axis may not be coincident with the sensing element axis. The electrical harness subassembly includes a metallic shield which includes electrical terminals therewithin which make electrical contact with the sensing element, and consequently, the sensing element is laterally supported by the shield at a second axial location along the sensing element axis. The shield extends along a shield axis and is joined to the shell at a radial interface between the shield and shell, and consequently, the shield axis and the shell axis are forced into alignment. However, due to manufacturing tolerances and variations, the sensing element axis may not be coincident with the shell axis and the electrical terminals may not be aligned with the sensing element, thereby resulting in a lateral force being induced on the sensing element. The sensing element is fragile and the lateral force may have negative effects on the sensing element which may be immediate or may develop after the gas sensor is placed in service.

What is needed is a gas sensor which minimizes or eliminates one or more of the shortcomings as set forth above.

SUMMARY OF THE INVENTION

Briefly described, a gas sensor is provided which includes a metallic shell extending along a shell axis and defining a shell attaching surface; a metallic shield extending along a shield axis and defining a shield attaching surface; and a ceramic sensing element extending along a sensing element axis, the sensing element being rigidly fixed at a first axial location of the sensing element to the shell and the sensing element being laterally supported by the shield at a second axial location of the sensing element that is axially spaced apart from the first axial location. The shield is attached to the shell at an interface formed between the shield attaching surface and the shell attaching surface such that misalignment between shield axis and the shell axis is accommodated, thereby minimizing stress on the sensing element.

A method of making a gas sensor is also provided where the method includes providing a metallic shell extending along a shell axis and defining a shell attaching surface; providing a metallic shield extending along a shield axis and defining a shield attaching surface; providing a ceramic sensing element extending along a sensing element axis; rigidly fixing the sensing element to the shell at a first axial location of the sensing element; laterally supporting the sensing element with the shield at a second axial location of the sensing element that is axially spaced apart from the first axial location; and attaching the shield to the shell at an interface formed between the shield attaching surface and the shell attaching surface such that misalignment between shield axis and the shell axis is accommodated, thereby minimizing stress on the sensing element.

Further features and advantages of the invention will appear more clearly on a reading of the following detailed description of the preferred embodiment of the invention, which is given by way of non-limiting example only and with reference to the accompanying drawings.

BRIEF DESCRIPTION OF DRAWINGS

This invention will be further described with reference to the accompanying drawings in which.

DETAILED DESCRIPTION OF INVENTION

Figure 1:
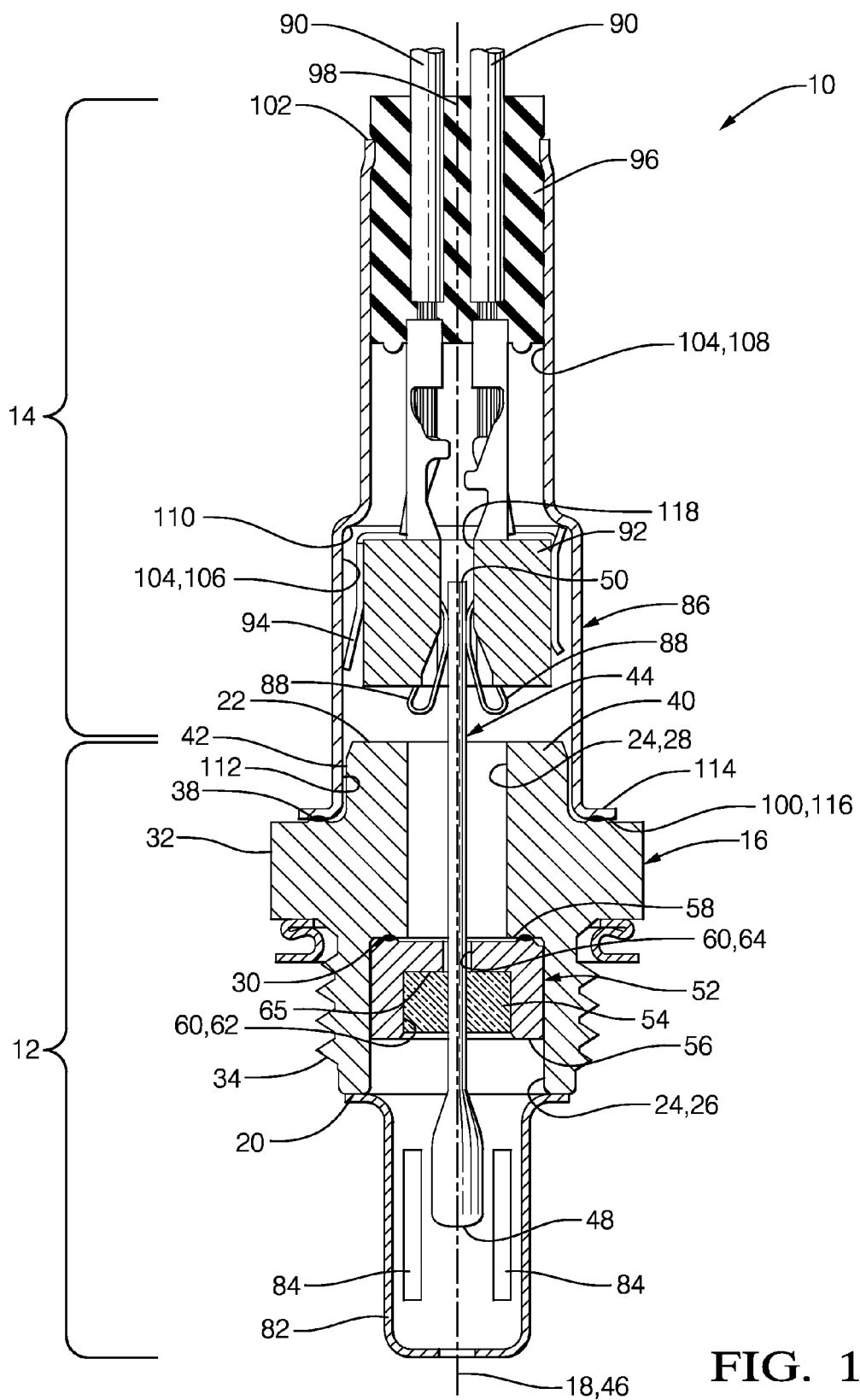
FIG. 1 is an axial cross-sectional view of a gas sensor in accordance with the present invention.

In accordance with a preferred embodiment of this invention and referring to FIG. 1, a gas sensor 10 is shown which generally includes a sensing subassembly 12 and an electrical harness subassembly 14. Gas sensor 10 is arranged to sense constituents of hot gases, by way of non-limiting example only, oxygen concentration levels of exhaust gases in an exhaust conduit (not shown) of an internal combustion engine (not shown).

Sensing subassembly 12 includes a metallic shell 16 which may be made of, for example only, 400 series stainless steel and which extends along a shell axis 18 from a shell first end 20 that is distal from electrical harness subassembly 14 to a shell second end 22 that is proximal to electrical harness subassembly 14.

A shell aperture 24 extends axially through shell 16 from shell first end 20 to shell second end 22 such that shell aperture 24 is centered about shell axis 18. Shell aperture 24 includes a shell aperture first section 26 which extends part way into shell 16 from shell first end 20 and a shell aperture second section 28 which extends from shell aperture first section 26 to shell second end 22. Shell aperture first section 26 is larger in diameter than shell aperture second section 28, consequently, a shell shoulder 30 is defined where shell aperture first section 26 meets shell aperture second section 28 such that shell shoulder 30 is substantially perpendicular to shell axis 18.

A shell flange 32 extends radially outward from shell 16. Shell flange 32 may aid in mounting gas sensor 10 to the exhaust conduit and may also aid in attaching electrical harness subassembly 14 to shell 16 as will be described in greater detail later. The outer perimeter of shell 16 between shell first end 20 and shell flange 32 may be provided with external threads 34 which may be used to mate with corresponding internal threads (not shown) of the exhaust conduit for mounting gas sensor 10 to the exhaust conduit. The outer perimeter of shell flange 32 may be a hex-shape in order to facilitate engagement by a tool that is used to rotate shell 16 when mating external threads 34 with the internal threads of the exhaust conduit. The side of shell flange 32 that is proximal to shell second end 22 defines a shell attaching surface 38 that lies in a plane that is substantially perpendicular to shell axis 18. A shell extension 40 may extend axially away from shell flange 32 to shell second end 22. Shell extension 40 is cylindrical and centered about shell axis 18, thereby defining an external diameter 42.

Sensing subassembly 12 also includes a ceramic sensing element 44 which extends along a sensing element axis 46 from a sensing element sensing end 48 to a sensing element terminal end 50. As shown in FIG. 1, sensing element axis 46 is coincident with shell axis 18; however, sensing element axis 46 may not be coincident with shell axis 18 due to manufacturing tolerances and variations. Sensing element 44 may be any cross-sectional shape (as sectioned perpendicular to sensing element axis 46), however, may preferably be rectangular in cross-sectional shape. Sensing element sensing end 48 is exposed, in use, to the gas being sensed while sensing element terminal end 50 is fluidly isolated from the gas being sensed as will be described in greater detail later. Sensing element terminal end 50 may be fluidly isolated from sensing element sensing end 48 in order for sensing element terminal end 50 to be exposed to an air reference zone. Sensing element 44 may be, by way of non-limiting example only, a sensing element as described in U.S. Pat. No. 7,827,848 to Kuisell et al., the disclosure of which is incorporated herein by reference in its entirety. Sensing element 44 is rigidly fixed to shell 16 at a first axial location of sensing element 44 as will be describe in greater detail in the paragraphs that follow.

In order to fluidly isolate sensing element terminal end 50 from sensing element sensing end 48 and to rigidly fix sensing element 44 to shell 16, sensing subassembly 12 includes a metallic glass holder 52 and a glass seal 54. Glass holder 52 is cylindrical and extends axially from a glass holder first end 56 to a glass holder second end 58. A glass holder aperture 60 extends axially through glass holder 52 and includes a glass holder aperture first section 62 which extends part way into glass holder 52 from glass holder first end 56 and a glass holder aperture second section 64 which extends from glass holder aperture first section 62 to glass holder second end 58. Glass holder aperture first section 62 is larger in cross-sectional area (as sectioned perpendicular to shell axis 18) than the cross-sectional area of glass holder aperture second section 64 (as sectioned perpendicular to shell axis 18), consequently, a glass holder shoulder 65 is defined where glass holder aperture first section 62 meets glass holder aperture second section 64. Glass holder aperture first section 62 may be cylindrical while glass holder aperture second section 64 may be shaped to match the cross-sectional shape of sensing element 44. Glass holder aperture second section 64 is sized to surround sensing element 44 sufficiently close to accommodate the forming of glass seal 54 as will be described in greater detail later.

Glass holder 52 may be sized to fit within shell aperture first section 26 in a slip fit interface such that glass holder 52 can be inserted into shell aperture first section 26 substantially uninhibited while substantially preventing radial movement of glass holder 52 within shell aperture first section 26. In order to prevent gases from migrating past shell aperture first section 26 between metallic glass holder 52 and shell aperture first section 26, glass holder 52 is metallurgically sealed to shell 16. As shown in the figures, glass holder 52 is metallurgically sealed to shell 16 at an axial interface between glass holder 52 and shell shoulder 30. In a preferred embodiment, glass holder 52 is metallurgically sealed to shell 16 by welding, and even more preferably by projection welding as will be described in greater detail in the paragraphs that follow.

Figure 2:
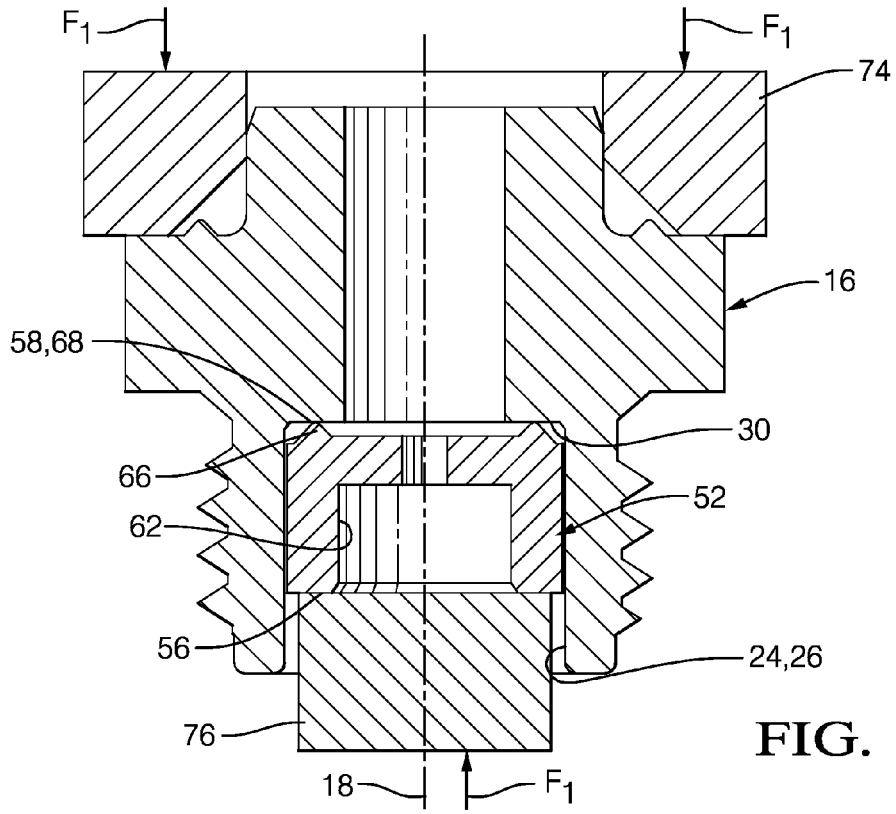
FIG. 2 is an enlarged axial cross-sectional view of a glass holder and a shell of the gas sensor in accordance with the present invention prior to projection welding the glass holder to the shell.
Figure 3:
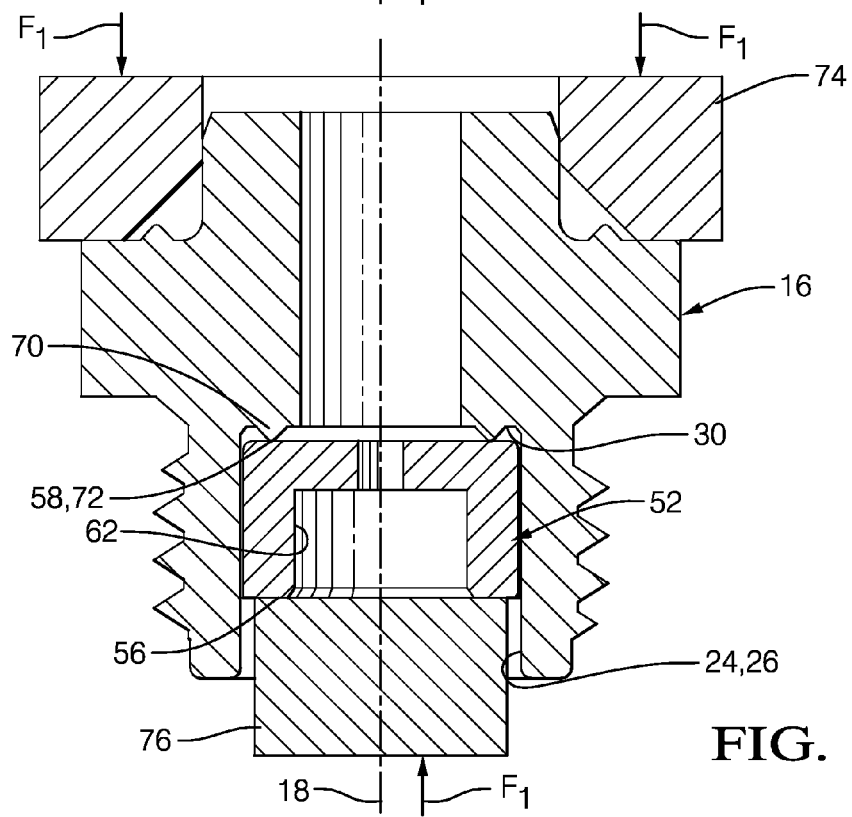
FIG. 3 is a variation of FIG. 2.

Referring now to FIGS. 2 and 3, in order to facilitate projection welding glass holder 52 to shell 16, either glass holder 52 or shell 16 includes a projection. As shown in FIG. 2, glass holder 52 (shown prior to being projection welded to shell 16) is provided with a projection 66 which is annular in shape and which comes to a point 68. Also as shown in FIG. 2, projection 66 may be defined at glass holder second end 58. Since projection 66 and glass holder aperture first section 62 are formed on opposite sides of glass holder 52, such an arrangement may be particularly conducive of manufacturing glass holder 52 by powder metal process or metal injection molding where powder metal is shaped in a mold and subsequently sintered in order to bind the particles of metal together. However, if glass holder 52 is desired to be made by machining from solid stock, projection 66 may be moved to glass holder first end 56 which allows projection 66 to be formed on the same side of glass holder 52 as glass holder aperture first section 62 which may be more desirable when machining glass holder 52 from solid stock. If projection 66 is formed on the same side of glass holder 52 as glass holder aperture first section 62, then glass holder 52 needs to be oriented in shell aperture first section 26 such that that glass holder first end 56 faces shell shoulder 30. Alternatively, as shown in FIG. 3, projection 66 is omitted from glass holder 52 and shell shoulder 30 is provided with a projection 70 which is annular in shape and which comes to a point 72.

In order to complete the projection weld between glass holder 52 and shell 16, a first welding electrode 74 is applied to shell 16 while a second welding electrode 76 is applied to glass holder 52 and projection 66 is place in contact with shell shoulder 30 (FIG. 2) or projection 70 is brought into contact with glass holder 52 (FIG. 3). Next, an electric current is passed between first welding electrode 74 and second welding electrode 76, consequently passing the electric current through shell 16 and glass holder 52. A compressive force is applied to projection 66 or projection 70 simultaneously with the passing of electric current through shell 16 and glass holder 52. The compressive force may be applied to projection 66 or projection 70 through one or both of first welding electrode 74 and second welding electrode 76 as represented by arrows $F_1$. The electric current produces heat at projection 66 or projection 70 and the compressive force collapses projection 66 or projection 70, thereby metallurgically sealing glass holder 52 to shell 16. Projection 66 or projection 70 may be collapsed by about 80% of the original height (in the direction of shell axis 18).

Figure 4:
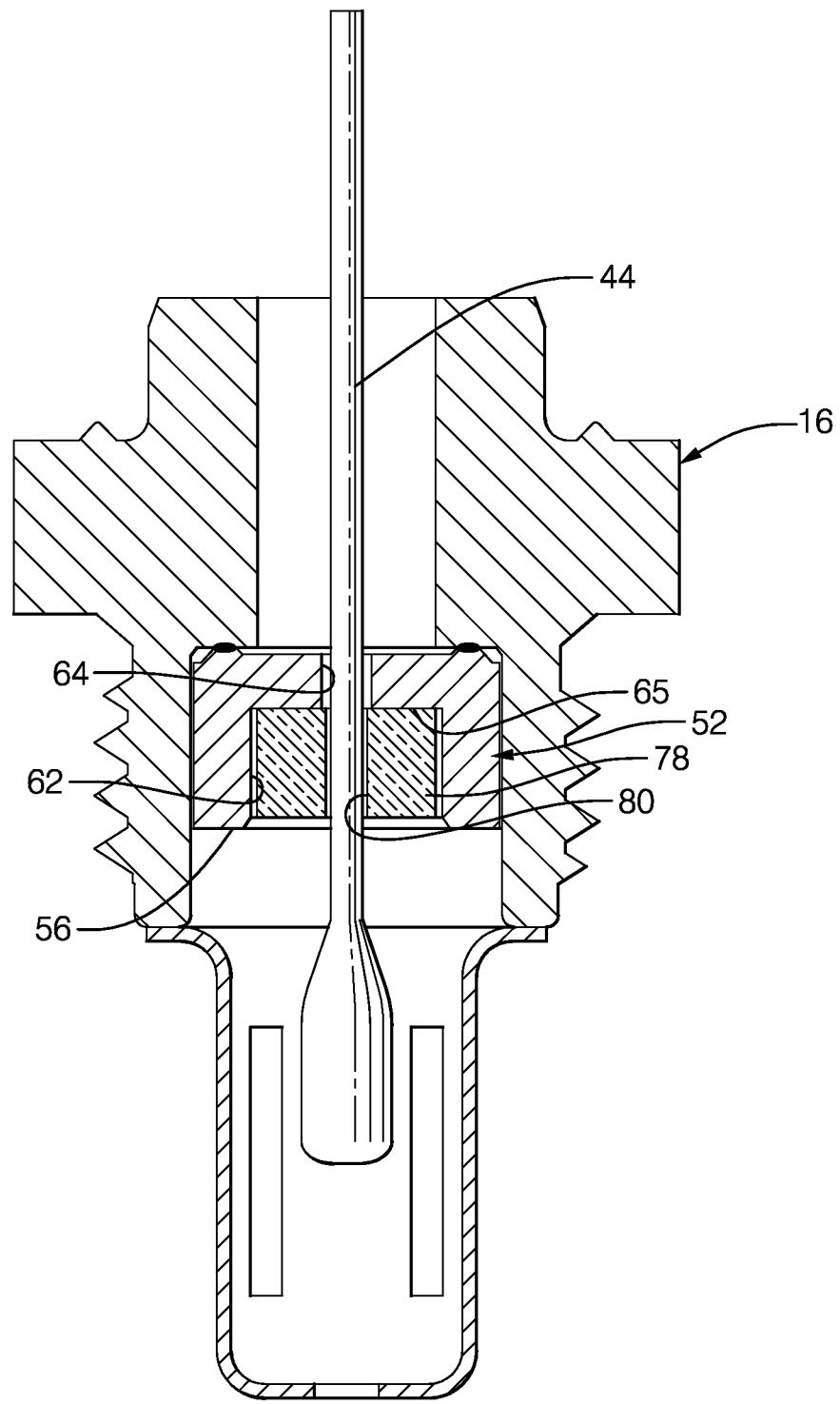
FIG. 4 is an enlarged axial cross-sectional view showing a portion of the gas sensor and a glass preform that is used to form a glass seal in the gas sensor in accordance with the present invention.

Now with reference to FIGS. 1 and 4, in order to form glass seal 54, a glass preform 78 is provided which includes a glass preform aperture 80 extending therethrough. Glass preform 78 is sized to be received within glass holder aperture first section 62 and glass preform aperture 80 is sized to receive sensing element 44 therethrough. Preferably, sensing element 44 is inserted into glass preform aperture 80 and then glass preform 78 is disposed in glass holder aperture first section 62 such that sensing element 44 extends through glass holder aperture second section 64, however, it should now be understood that sensing element 44 may first be disposed within glass holder aperture second section 64 and then glass preform 78 may next be disposed within glass holder aperture first section 62 such that sensing element 44 extends through glass preform aperture 80. After sensing element 44 is positioned at the desired axial position relative to shell 16, glass preform 78 is heated to a sufficiently high temperature to allow glass preform 78 to become molten glass and flow and conform to sensing element 44, glass holder aperture first section 62, and glass holder shoulder 65. Glass preform 78 may be heated, by way of non-limiting example only, by an induction heating coil (not shown) that radially surrounds shell 16. It should be noted that the clearance between sensing element 44 and glass holder aperture second section 64 is sufficiently small in order to prevent glass preform 78 from escaping between sensing element 44 and glass holder aperture second section 64 when glass preform 78 is heated to allow it to flow. After allowing the molten glass to cool, thereby forming glass seal 54, glass seal 54 forms a hermetic seal with glass holder 52 and sensing element 44. The material of glass seal 54 is selected to be compatible with the high temperature environment that glass seal 54 will be exposed to in use. Glass seal 54 preferably has a coefficient of thermal expansion that is less than the coefficient of thermal expansion of glass holder 52.

Again with reference to FIG. 1, sensing subassembly 12 also includes a lower shield 82 which protects sensing element 44 from damage during installation of gas sensor 10 to the exhaust conduit and from damage during operation due high exhaust gas velocities and particulate that may be present in the exhaust gas. Lower shield 82 is made of metal, preferably stainless steel, and may be made, for example, by deep drawing. Lower shield 82 includes a plurality of lower shield louvers 84 therethrough in order to allow the gas to be sensed to be communicated to sensing element sensing end 48. Lower shield 82 may be attached to shell first end 20, for example, by crimping or welding.

Electrical harness subassembly 14 includes an upper shield 86; a plurality of electrical terminals 88 each having a corresponding wire 90 extending therefrom and providing electrical communication between sensing element 44 and an electronic device (not shown), for example only, an electronic control unit of a motor vehicle; a connector body 92; a retainer 94; and a sealing member 96.

Upper shield 86 may be made of, for example only, 400 series stainless steel which extends along an upper shield axis 98 from an upper shield first end 100 that is proximal to shell 16 to an upper shield second end 102 that is distal from shell 16.

An upper shield aperture 104 extends axially through upper shield 86 from upper shield first end 100 to upper shield second end 102 such that upper shield aperture 104 is centered about upper shield axis 98. Upper shield aperture 104 includes an upper shield aperture first section 106 which extends part way into upper shield 86 from upper shield first end 100 and an upper shield aperture second section 108 which extends from upper shield aperture first section 106 to upper shield second end 102. Upper shield aperture first section 106 is larger in diameter than upper shield aperture 104, consequently an upper shield shoulder 110 is defined where upper shield aperture first section 106 meets upper shield aperture 104. Upper shield aperture first section 106 defines an internal diameter 112 that radially surrounds shell extension 40 such that internal diameter 112 is larger than external diameter 42, the importance of which will be made readily apparent later.

An upper shield flange 114 extends radially outward from upper shield 86 at upper shield first end 100. The side of upper shield flange 114 that faces toward shell 16 defines an upper shield attaching surface 116 that is substantially perpendicular to upper shield axis 98. Upper shield flange 114 is used to attach electrical harness subassembly 14 to shell 16 as will be described in greater detail later.

Connector body 92 is made of an electrically insulative material, for example ceramic, and includes a connector body aperture 118 that extends through connector body 92 in the same general direction as upper shield axis 98. Connector body 92 is configured to hold electrical terminals 88 such that electrical terminals 88 extend into connector body aperture 118.

Retainer 94 may be made of metal and radially surrounds connector body 92. Retainer 94 grips the outer perimeter of connector body 92 and has features which are elastically deformed when retainer 94 and connector body 92 are inserted into upper shield aperture first section 106 until retainer 94 reaches upper shield shoulder 110. Consequently, retainer 94 prevents movement of connector body 92 within upper shield 86. It should be noted that retainer 94 may hold connector body 92 in such a way that connector body aperture 118 and electrical terminals 88 may not be centered about shell axis 18 or upper shield axis 98.

Sealing member 96 is preferably made from an elastomeric material and is disposed within upper shield aperture second section 108. Wires 90 pass through sealing member 96 such that each wire 90 is individually sealed with sealing member 96. Upper shield 86 may be radially crimped around sealing member 96, thereby allowing sealing member 96 to prevent intrusion of water and other contaminants from entering upper shield 86.

Sensing element terminal end 50 is received within connector body aperture 118 such that sensing element terminal end 50 elastically displaces electrical terminals 88 in order to provide reliable electrical contact with mating terminals (not shown) on sensing element 44. In this way, sensing element 44 is laterally supported by upper shield 86 at a second axial location of sensing element 44 that is axially apart from the axial location where sensing element 44 is rigidly fixed to shell 16.

Due to manufacturing tolerances and variations, shell axis 18, sensing element axis 46, and upper shield axis 98 may not always be coincident to one another. Consequently, if upper shield 86 is fixed to shell 16 in a concentric relationship such that shell axis 18 is coincident with upper shield axis 98, stress may be placed laterally on sensing element 44. In order to minimize or eliminate lateral stress on sensing element 44, upper shield 86 is attached to shell 16 using upper shield attaching surface 116 and shell attaching surface 38. Since upper shield attaching surface 116 is substantially perpendicular to upper shield axis 98 and shell attaching surface 38 is substantially perpendicular to shell axis 18, misalignment between upper shield axis 98 and shell axis 18 is accommodated while still allowing upper shield attaching surface 116 and shell attaching surface 38 to be joined together as will be described below. As described previously, internal diameter 112 of upper shield aperture first section 106 is larger than external diameter 42 of shell extension 40. This relationship accommodates the necessary misalignment between upper shield axis 98 and shell axis 18. Of course, the magnitude of allowable misalignment between upper shield axis 98 and shell axis 18 is determined by the difference in size between internal diameter 112 of upper shield aperture first section 106 and external diameter 42 of shell extension 40. Consequently, the difference in size between internal diameter 112 of upper shield aperture first section 106 and external diameter 42 of shell extension 40 is preferably designed to accommodate the maximum amount of misalignment between upper shield axis 98 and shell axis 18 that would be necessary to allow insertion of sensing element 44 into connector body aperture 118 while applying no lateral stress or an acceptable magnitude of lateral stress to sensing element 44.

Figure 5:
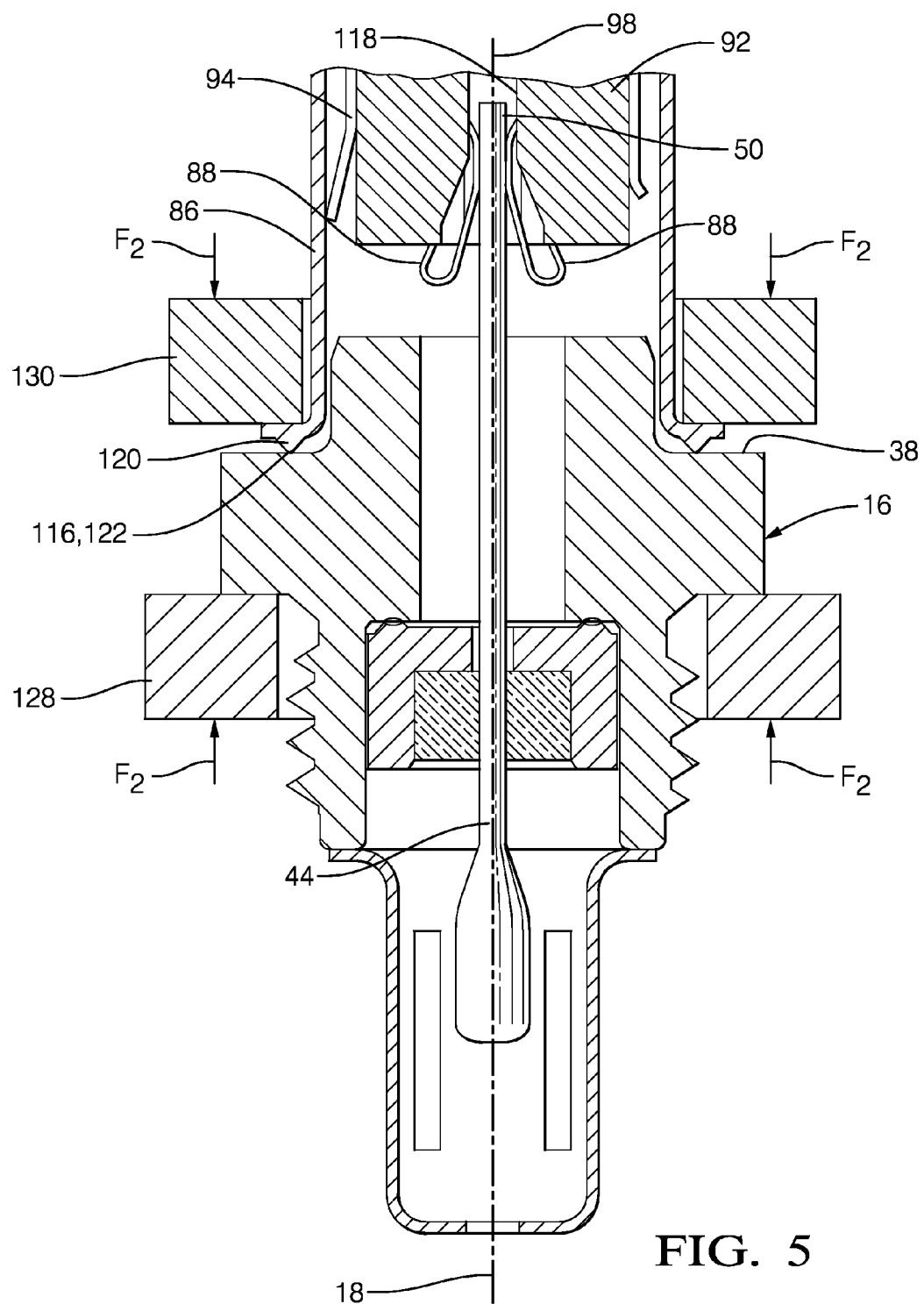
FIG. 5 is an enlarged axial cross-sectional view of an upper shield and a shell of the gas sensor in accordance with the present invention prior to projection welding the upper shield to the shell.
Figure 6:
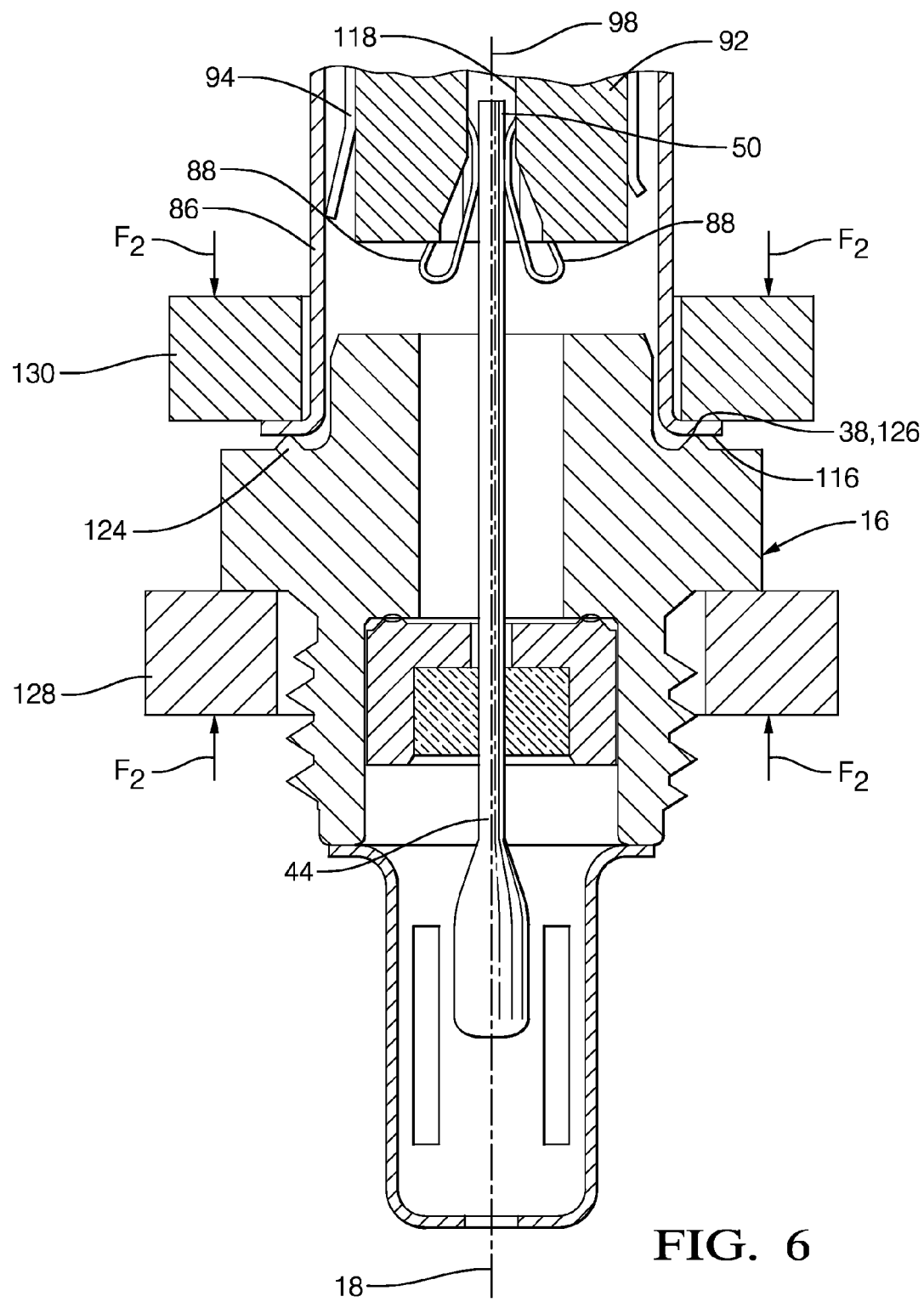
FIG. 6 is a variation of FIG. 5.

Referring now to FIGS. 5 and 6, a method will now be describe for attaching upper shield 86 to shell 16. Prior to attaching upper shield 86 to shell 16; sensing element 44 is already rigidly fixed to shell 16 as described above. Also prior to attaching upper shield 86 to shell 16, electrical terminals 88, wires 90, connector body 92, retainer 94, and sealing member 96 are positioned within upper shield 86 as described above. Next, sensing element terminal end 50 is inserted into connector body aperture 118, thereby elastically displacing electrical terminals 88 and making electrical contact between electrical terminals 88 and sensing element 44. Sensing element terminal end 50 is inserted into connector body aperture 118 until upper shield attaching surface 116 contacts shell attaching surface 38. The relative position of upper shield axis 98 and shell axis 18 is allowed to be determined by sensing element 44 and electrical terminals 88, thereby preventing excessive lateral stress from being applied to sensing element 44 by upper shield 86 which now laterally supports sensing element 44. After sensing element 44 and electrical terminals 88 determine the relative position of upper shield axis 98 and shell axis 18, upper shield 86 is attached to shell 16 at an interface formed between upper shield attaching surface 116 and shell attaching surface 38, for example, by metallurgical bonding. Projection welding may be used in a preferred embodiment of attaching upper shield 86 to shell 16 at an interface formed between upper shield attaching surface 116 and shell attaching surface 38. As shown in FIG. 5 upper shield attaching surface 116 is further defined by an annular projection 120 which extends axially from upper shield flange 114 toward shell attaching surface 38 and comes to a point 122. Alternatively, as shown in FIG. 6, projection 120 is omitted from upper shield flange 114 and shell attaching surface 38 is further defined by an annular projection 124 which extends axially from shell flange 32 toward upper shield 86 and comes to a point 126.

In order to complete the projection weld between upper shield 86 and shell 16, a third welding electrode 128 is applied to shell 16 while a fourth welding electrode 130 is applied to upper shield 86 and projection 120 is placed in contact with shell attaching surface 38 (FIG. 5) or projection 124 is brought into contact with upper shield attaching surface 116 (FIG. 6). Next, an electric current is passed between third welding electrode 128 and fourth welding electrode 130, consequently the electric current passes through shell 16 and upper shield 86. A compressive force is applied to projection 120 or projection 124 simultaneously with the passing of electric current through shell 16 and upper shield 86. The compressive force may be applied to projection 120 or projection 124 through one or both of third welding electrode 128 and fourth welding electrode 130 as represented by arrows $F_2$. The electric current produces heat at projection 120 or projection 124 and the compressive force collapses projection 120 or projection 124, thereby metallurgically boding upper shield 86 to shell 16. Projection 120 or projection 124 may be collapsed by about 80% of the original height (in the direction of upper shield axis 98).

While this invention has been described in terms of preferred embodiments thereof, it is not intended to be so limited, but rather only to the extent set forth in the claims that follow.

We claim:
1. A gas sensor comprising:
a metallic shell extending along a shell axis and defining a shell attaching surface;
a metallic shield extending along a shield axis and defining a shield attaching surface; and
a ceramic sensing element extending along a sensing element axis, said sensing element being rigidly fixed at a first axial location of said sensing element to said shell and said sensing element being laterally supported by said shield at a second axial location of said sensing element that is axially spaced apart from said first axial location;
wherein said shield is attached to said shell at an interface formed between said shield attaching surface and said shell attaching surface such that misalignment between said shield axis and said shell axis is accommodated, thereby minimizing stress on said sensing element.
2. A gas sensor as in claim 1 wherein said shield attaching surface is metallurgically bonded to said shell attaching surface.
3. A gas sensor as in claim 1 wherein:
said shell attaching surface is substantially perpendicular to said shell axis; and
said shield attaching surface is substantially perpendicular to said shield axis.
4. A gas sensor as in claim 3 wherein said shield comprises:
a shield aperture within which said sensing element is laterally supported; and
an annular shield flange extending radially outward therefrom, wherein said shield flange defines said shield attaching surface.
5. A gas sensor as in claim 4 wherein said shield attaching surface is further defined by an annular projection which extends axially from said shield flange toward said shell attaching surface.
6. A gas sensor as in claim 5 wherein said projection is projection welded to said shell attaching surface.
7. A gas sensor as in claim 1 wherein said sensing element is laterally supported within said shield by an electrical connector assembly that is in electrical contact with said sensing element.
8. A gas sensor as in claim 4 wherein:
said shield aperture defines an internal diameter; and
said shell includes a cylindrical shell extension extending into said shield aperture and defines an external diameter that is smaller than said internal diameter of said shield aperture, thereby accommodating misalignment between said shield axis and said shell axis.
9. A gas sensor as in claim 4 wherein said shell attaching surface is defined by an annular projection which extends axially from said shell toward said shield attaching surface.
10. A gas sensor as in claim 9 wherein said projection is projection welded to said shield attaching surface.
11. A method of making a gas sensor, said method comprising:

providing a metallic shell extending along a shell axis and defining a shell attaching surface;

providing a metallic shield extending along a shield axis and defining a shield attaching surface;

providing a ceramic sensing element extending along a sensing element axis;

rigidly fixing said sensing element to said shell at a first axial location of said sensing element;

laterally supporting said sensing element with said shield at a second axial location of said sensing element that is axially spaced apart from said first axial location;

attaching said shield to said shell at an interface formed between said shield attaching surface and said shell attaching surface such that misalignment between said shield axis and said shell axis is allowed, thereby minimizing stress on said sensing element.

12. A method as in claim 11 wherein said step of attaching said shield to said shell comprises metallurgically bonding said shield attaching surface to said shell attaching surface.

13. A method as in claim 11 wherein:
said shell attaching surface is substantially perpendicular to said shell axis; and
said shield attaching surface is substantially perpendicular to said shield axis.

14. A method as in claim 13 wherein said shield comprises:
a shield aperture within which said sensing element is laterally supported; and
an annular shield flange extending radially outward therefrom, wherein said shield flange defines said shield attaching surface.

15. A method as in claim 14 wherein said shield attaching surface is further defined by an annular projection which extends axially from said shield flange toward said shell attaching surface.

16. A method as in claim 15 wherein said step of attaching said shield to said shell comprises:

placing said projection in contact with said shell attaching surface; and passing an electric current through said shield and said shell and simultaneously applying a compressive force to said projection, thereby creating heat at said projection and collapsing said projection in order to metallurgically bond said shield to said shell.

17. A method as in claim 11 wherein said step of laterally supporting said sensing element with said shield includes using an electrical connector assembly that is in electrical contact with said sensing element to laterally support said sensing element with said shield.

18. A method as in claim 14 wherein:
said shield aperture defines an internal diameter;
said shell includes a cylindrical shell extension defining an external diameter that is smaller than said internal diameter of said shield aperture;
said method further comprises inserting said shell extension into said shield aperture such that said shell extension within said shield aperture accommodates misalignment between said shield axis and said shell axis.

19. A method as in claim 14 wherein said shell attaching surface is defined by an annular projection which extends axially from said shell toward said shield attaching surface.

20. A method as in claim 19 wherein said step of attaching said shield to said shell comprises:

placing said projection in contact with said shield attaching surface; and passing an electric current through said shield and said shell and simultaneously applying a compressive force to said projection, thereby creating heat at said projection and collapsing said projection in order to metallurgically bond said shield to said shell.

* * * * *